US007947654B2

(12) United States Patent
Nilsson et al.

(10) Patent No.: US 7,947,654 B2
(45) Date of Patent: *May 24, 2011

(54) PHARMACEUTICAL FORMULATIONS

(75) Inventors: Anders Nilsson, Lund (SE); Hans Lindner, Leichlingen (DE); Jørgen Wittendorff, Hvidovre (DK)

(73) Assignee: Ferring B.V., Hoofddorp (NL)

( * ) Notice: Subject to any disclaimer, the term of this patent is extended or adjusted under 35 U.S.C. 154(b) by 236 days.

This patent is subject to a terminal disclaimer.

(21) Appl. No.: 12/487,116

(22) Filed: Jun. 18, 2009

(65) Prior Publication Data

US 2009/0318665 A1    Dec. 24, 2009

Related U.S. Application Data

(63) Continuation of application No. 10/513,437, filed as application No. PCT/IB03/02368 on May 7, 2003, now Pat. No. 7,560,429.

(30) Foreign Application Priority Data

May 7, 2002 (GB) .................................. 0210397.6
Sep. 20, 2002 (WO) ........................ PCT/IB02/04036

(51) Int. Cl.
*A61K 38/12* (2006.01)

(52) U.S. Cl. ....... 514/21.1; 514/21.7; 530/317; 530/328

(58) Field of Classification Search .................. None
See application file for complete search history.

(56) References Cited

U.S. PATENT DOCUMENTS

| | | |
|---|---|---|
| 4,263,283 A | 4/1981 | Cort |
| 4,285,858 A | 8/1981 | Cort et al. |
| 4,588,580 A | 5/1986 | Gale et al. |
| 4,731,360 A | 3/1988 | Alexander et al. |
| 4,764,378 A | 8/1988 | Keith et al. |
| 4,863,737 A | 9/1989 | Stanley et al. |
| 4,878,892 A | 11/1989 | Sibalis et al. |
| 5,047,398 A | 9/1991 | Hagstam et al. |
| 5,091,186 A | 2/1992 | Miranda et al. |
| 5,135,480 A | 8/1992 | Bannon et al. |
| 5,298,256 A | 3/1994 | Flockhart et al. |
| 5,466,464 A | 11/1995 | Masaki et al. |
| 5,482,931 A | 1/1996 | Harris et al. |
| 5,498,598 A | 3/1996 | Harris et al. |
| 5,500,413 A | 3/1996 | Larsson et al. |
| 5,596,078 A | 1/1997 | Andersson et al. |
| 5,631,246 A | 5/1997 | Hashemi et al. |
| 5,674,850 A | 10/1997 | Larsson et al. |
| 5,698,516 A | 12/1997 | Nilsson et al. |
| 5,707,648 A | 1/1998 | Yiv |
| 5,726,287 A | 3/1998 | Andersson et al. |
| 5,763,398 A | 6/1998 | Bengtsson et al. |
| 5,763,405 A | 6/1998 | Fjellestad-Paulsen et al. |
| 5,763,407 A | 6/1998 | Larsson et al. |
| 5,780,434 A | 7/1998 | Fjellestad-Paulsen et al. |
| 5,843,016 A | 12/1998 | Lugnani et al. |
| 5,848,991 A | 12/1998 | Gross et al. |
| 5,849,322 A | 12/1998 | Gutniak et al. |
| 5,906,831 A | 5/1999 | Larsson et al. |
| 5,922,680 A | 7/1999 | Fjellestad-Paulsen et al. |
| 5,929,027 A | 7/1999 | Takama et al. |
| 5,932,745 A | 8/1999 | Dushin et al. |
| 5,948,433 A | 9/1999 | Burton et al. |
| 5,985,385 A | 11/1999 | Gottfried |
| 5,985,835 A | 11/1999 | Larsson et al. |
| 5,990,273 A | 11/1999 | Andersson et al. |
| 6,010,478 A | 1/2000 | Bellhouse et al. |
| 6,090,803 A | 7/2000 | Failli et al. |
| 6,139,866 A | 10/2000 | Chono et al. |
| 6,143,722 A | 11/2000 | Melin et al. |
| 6,194,407 B1 | 2/2001 | Failli et al. |
| 6,235,900 B1 | 5/2001 | Failli et al. |
| 6,248,363 B1 | 6/2001 | Patel et al. |
| 6,264,981 B1 | 7/2001 | Zhang et al. |
| 6,268,360 B1 | 7/2001 | Failli et al. |
| 6,297,234 B1 | 10/2001 | Failli et al. |
| 6,314,317 B1 | 11/2001 | Willis |
| 6,322,532 B1 | 11/2001 | D'Sa et al. |
| 6,344,451 B1 | 2/2002 | Steffan et al. |
| 6,348,486 B1 | 2/2002 | Argentieri et al. |
| 6,406,455 B1 | 6/2002 | Willis et al. |
| 6,490,483 B2 | 12/2002 | Willis |
| 6,509,040 B1 | 1/2003 | Murray et al. |
| 6,511,974 B1 | 1/2003 | Dusza et al. |

(Continued)

FOREIGN PATENT DOCUMENTS

| | | |
|---|---|---|
| EP | 0 517 211 A | 12/1992 |
| EP | 1153616 | 11/2001 |
| GB | 1 548 022 | 7/1979 |
| GB | 2 111 423 A | 7/1983 |
| GB | 2 114 440 A | 8/1983 |
| WO | WO-85/02119 A1 | 5/1985 |
| WO | WO-94/12142 A1 | 6/1994 |
| WO | WO-95/01185 A1 | 1/1995 |
| WO | WO 97/15297 | 5/1997 |
| WO | WO-00/36353 A1 | 6/2000 |
| WO | WO 00 44351 A | 8/2000 |
| WO | WO 00 59423 A | 10/2000 |
| WO | WO 00 61117 A | 10/2000 |
| WO | WO-01/60394 A1 | 8/2001 |
| WO | WO-02/074286 A1 | 9/2002 |
| WO | WO-03/094885 A1 | 11/2003 |

(Continued)

OTHER PUBLICATIONS

Dobetti, Luca. Fast-Melting Tablets: Developments and Technologies. Pharmaceutical Technology Drug Delivery 2001, pp. 44-50.*

(Continued)

*Primary Examiner* — Anish Gupta
(74) *Attorney, Agent, or Firm* — Foley & Lardner LLP

(57) ABSTRACT

Good bioavailability of desmopressin can be obtained by means of an orodispersible pharmaceutical dosage form. Preferred dosage forms comprise desmopressin and an open matrix network which is an inert water-soluble or water-dispersible carrier material. Desmopressin formulated in this way is useful for voiding postponement, or the treatment or prevention of incontinence, primary nocturnal enuresis (PNE), nocturia or central diabetes insipidus. Peptides other than desmopressin can also be formulated in this way.

9 Claims, No Drawings

U.S. PATENT DOCUMENTS

| | | |
|---|---|---|
| 6,616,627 B2 | 9/2003 | Willis et al. |
| 6,620,807 B1 | 9/2003 | Steffan et al. |
| 6,664,249 B1 | 12/2003 | Ashworth et al. |
| 6,693,082 B2 | 2/2004 | Alonso et al. |
| 6,720,001 B2 | 4/2004 | Chen et al. |
| 6,746,678 B1 | 6/2004 | Shapiro |
| 6,903,091 B2 | 6/2005 | Failli et al. |
| 6,939,324 B2 | 9/2005 | Gonnelli et al. |
| 6,945,952 B2 | 9/2005 | Kwon |
| 6,960,184 B2 | 11/2005 | Willis et al. |
| 7,018,653 B2 | 3/2006 | Wannerberger et al. |
| 7,022,340 B2 | 4/2006 | Lomryd et al. |
| 7,022,699 B2 | 4/2006 | Failli et al. |
| 7,027,478 B2 | 4/2006 | Ackley |
| 7,053,083 B2 | 5/2006 | Failli et al. |
| 7,060,708 B2 | 6/2006 | Piccariello et al. |
| 7,074,781 B2 | 7/2006 | Ashworth et al. |
| 7,094,545 B2 | 8/2006 | Lomryd et al. |
| 7,097,631 B2 | 8/2006 | Trautman et al. |
| 7,138,393 B2 | 11/2006 | Molinari et al. |
| 7,150,409 B2 | 12/2006 | Gonnelli et al. |
| 7,153,845 B2 | 12/2006 | Levine et al. |
| 7,182,747 B2 | 2/2007 | Kwon |
| 7,187,969 B2 | 3/2007 | Willis |
| 7,405,203 B2 | 7/2008 | Fein |
| 7,560,429 B2 | 7/2009 | Nilsson et al. |
| 7,579,321 B2 | 8/2009 | Fein |
| 7,799,761 B2 | 9/2010 | Fein |
| 2002/0013262 A1 | 1/2002 | Alonso et al. |
| 2002/0107265 A1 | 8/2002 | Chen et al. |
| 2002/0128599 A1 | 9/2002 | Cormier et al. |
| 2002/0178196 A1 | 11/2002 | Monier |
| 2002/0198191 A1 | 12/2002 | Failli et al. |
| 2003/0018024 A1 | 1/2003 | Failli et al. |
| 2003/0087892 A1 | 5/2003 | Ashworth et al. |
| 2003/0119728 A1 | 6/2003 | Scheidl et al. |
| 2003/0134845 A1 | 7/2003 | Molinari et al. |
| 2004/0018241 A1 | 1/2004 | Houze et al. |
| 2004/0038962 A1 | 2/2004 | Ashworth et al. |
| 2004/0063628 A1 | 4/2004 | Piccariello et al. |
| 2004/0115167 A1 | 6/2004 | Cormier et al. |
| 2004/0138098 A1 | 7/2004 | Fein |
| 2004/0138610 A1 | 7/2004 | Cormier et al. |
| 2004/0220080 A1 | 11/2004 | Lomryd et al. |
| 2004/0242686 A1 | 12/2004 | Isawa et al. |
| 2004/0249339 A1 | 12/2004 | Willis et al. |
| 2004/0265365 A1 | 12/2004 | Daddona et al. |
| 2005/0004103 A1 | 1/2005 | Koshio et al. |
| 2005/0019392 A1 | 1/2005 | Lomryd et al. |
| 2005/0075328 A1 | 4/2005 | Failli et al. |
| 2005/0089554 A1 | 4/2005 | Cormier et al. |
| 2005/0096586 A1 | 5/2005 | Trautman et al. |
| 2005/0106226 A1 | 5/2005 | Cormier et al. |
| 2005/0153873 A1 | 7/2005 | Chan et al. |
| 2005/0154350 A1 | 7/2005 | Willis et al. |
| 2005/0158378 A1 | 7/2005 | Wannerberger et al. |
| 2005/0232997 A1 | 10/2005 | Nilsson et al. |
| 2006/0025387 A1 | 2/2006 | Hochman |
| 2006/0040970 A1 | 2/2006 | Izumimoto et al. |
| 2006/0093658 A1 | 5/2006 | Sathyan et al. |
| 2006/0122113 A1 | 6/2006 | Pinchasi et al. |
| 2006/0122170 A1 | 6/2006 | Koshio et al. |
| 2006/0154916 A1 | 7/2006 | Ashworth et al. |
| 2006/0183734 A1 | 8/2006 | Failli et al. |
| 2006/0189939 A1 | 8/2006 | Gonnelli et al. |
| 2006/0193825 A1 | 8/2006 | Musso et al. |
| 2006/0200069 A1 | 9/2006 | Cormier et al. |
| 2006/0240068 A1 | 10/2006 | Lomryd et al. |
| 2006/0241172 A1 | 10/2006 | Zhou et al. |
| 2006/0241176 A1 | 10/2006 | Stack et al. |
| 2006/0247276 A1 | 11/2006 | Gross et al. |
| 2006/0252696 A1 | 11/2006 | Lomryd et al. |
| 2006/0253061 A1 | 11/2006 | Anderson et al. |
| 2006/0258712 A1 | 11/2006 | Jacobson |
| 2006/0258714 A1 | 11/2006 | Heffernan et al. |
| 2006/0258739 A1 | 11/2006 | Ai et al. |
| 2007/0027427 A1 | 2/2007 | Trautman et al. |
| 2007/0032410 A1 | 2/2007 | Quay et al. |
| 2007/0117759 A1 | 5/2007 | Wannerberger et al. |
| 2008/0274951 A1 | 11/2008 | Fein |

FOREIGN PATENT DOCUMENTS

| | | |
|---|---|---|
| WO | WO-03/094886 A2 | 11/2003 |
| WO | WO-2004/041153 A2 | 5/2004 |
| WO | WO-03/094886 A3 | 7/2004 |
| WO | WO-2004/041153 A3 | 8/2004 |
| WO | WO-2005/046707 A1 | 5/2005 |

OTHER PUBLICATIONS

Ferring AB, "Minirin DDAVP (desmopressin)", *Official Gazette of the Italian Republic*, Decree No. 191, Mar. 5, 1993.

Scherer DDS, "ZYDIS—Fast Dissolving Dosage Form," product brochure issued 1994.

Stuttaford, "How to avoid the curse of bedwetting," *The Times* (London), Mar. 28, 2002.

U.S. Appl. No. 12/173,072, filed Jul. 15, 2008, Fein.

U.S. Appl. No. 12/173,074, filed Jul. 15, 2008, Fein.

"Minirin Nasal Spray". Ferring Pharmaceuticals. Internet document <<http://www.medsafe.gov.nz/Consumers/CMI/m/MinirinNSpray.htm>&g- t; May 3, 2001; accessed Sep. 15, 2008; 4 pages.

Doctoral Dissertation, "Absorption and Metabolism of Neurophypophyseal Hormones, with special reference to Desmopressin (dDAVP), in Human Tissue and after Various Routes of Administration", (Fjellestad-Paulsen, Anne M.) May 25, 1996.

Trinh-Trang-Tan et al. "Regulation of UT-A2 Protein in vivo and in vitro", Journal of the American Society of Nephrology, (Sep. 2000) vol. 11, Program and Abstract Issue, pp. 23A.

Wolfson Philip et al. (1979) "Mechanism of Vasopressin Inhibition of Pancreatic Secretion", American Journal of Gastroenterology, vol. 71, No. 5, pp. 490-495.

Jahr S Jonathan et al. (1992) "Effect of Desmopressin Acetate on Hindlimb Perfusion Pressure in Rats: What is the Mechanism?" Anesthesia & Analgesia, vol. 75, No. 3, pp. 411-415.

Dixon A.K. et al. (1981) "The Effect of DDAVP on Intravenous Urography", British Journal of Radiology, vol. 54, pp. 484-487.

Malan T. Philip et al. (1994) "Subcutaneous Administration of Desmopressin as a Test of Maximal Urinary Concentrating Ability in the Fischer 344 Rat", Toxicology Methods, vol. 4, No. 3, pp. 188-192.

Tormey William Patrick & O'Laoire Sean Arthur (1992) "Severe Prolonged Antidiuresis Following Desmopressin and Carbamazepine Interaction in Postoperative Diabetes Insipidus", European Journal of Internal Medicine, vol. 3, pp. 341-343.

Vilhardt H et al. (1986) "Plasma Kinetics of DDAVP in Man", Acta Pharmacol Toxicol (Copenh), 58 (5): 379-381.

International Search Report for PCT/IB2003/02368, issued Mar. 19, 2004.

Ashley Grossman et al., "Two new nodes of desmopressin (DDAVP) administration", British Medical Journal, May 17, 1980, p. 1215, XP002260408.

F. Laczi et al., "Effects of vasopressin analogues (DDAVP, DVDAVP) in the form of sublingual tablets in central diabetes insipidus", International Journal of Clinical Pharmacology: Therapy and Toxicology, vol. 18, No. 12, 1980, pp. 63-68 XP002260419.

Minirin® —Tablet package information (Ferring) (2000) (4 pgs.).

"Vidal 1997", 1997, Editions Du Vidal, Paris XP002277248, p. 1047-1048.

European Search Report May 10, 1994 (9 pgs.).

Non-Final Office Action dated Sep. 3, 2008 in U.S. Appl. No. 10/519,715. (13 pgs.).

Supplemental Notice of Allowability dated Apr. 24, 2009, in U.S. Appl. No. 10/513,437 (US 2005/0232997—parent application).

Notice of Allowance dated Feb. 4, 2009, in U.S. Appl. No. 10/513,437 (US 2005/0232997—parent application).

Advisory Action dated Aug. 7, 2008, in U.S. Appl. No. 10/513,437 (US 2005/0232997—parent application).

Office Action dated Nov. 15, 2007, in U.S. Appl. No. 10/513,437 (US 2005/0232997—parent application).

Office Action dated Mar. 27, 2007, in U.S. Appl. No. 10/513,437 (US 2005/0232997—parent application).

Chang et al., "Fast-Dissolving Tablets," *Pharmaceutical Technology*, pp. 52-58, Jun. 2000.

FDA Electronic Orange Book, "Active Ingredient Search Results from "OB_Rx" table for query on "loratadine"," http://www.accessdata.fda.gov/scripts/cder/ob/docs/temapi.cfm, accessed on Apr. 3, 2008.

Pfizer Limited, "Feldene Capsules, Feldene I.M. Intramuscular Injection, Feldene MELT," product information, http://emc.medicines.org.uk/emc/assets/c/html/displayDocPrinterFriendly.asp?document, accessed on Mar. 31, 2008.

Noehr-Jensen et al., "The relative bioavailability of loratadine administered as a chewing gum formulation in healthy volunteers," *European Journal of Clinical Pharmacology*, vol. 62, pp. 437-445, 2006.

Supervia et al., "Piroxicam fast-dissoloving dosage form vs diclofenac sodium in the treatment of acute renal colic: a double-blind controlled trial," *British Journal of Urology*, vol. 81, pp. 27-30, 1998.

Piscitelli et al., "The Impact of Formulation and Process Changes on in Vitro Dissolution and the Bioequivalence of Piroxicam Capsules," *Pharmaceutical Development and Technology*, vol. 3, No. 4, pp. 443-452, 1998.

Schering Corporation, "Clarinex®," product information, revised Feb. 2007.

Pfizer Limited, "Feldene™ Melt 20 mg," product information, revised Nov. 2009.

Jaccard et al., "A new galenic form: the lyoc," *Ann. pharmaceutiques francaises*, vol. 43, No. 2, pp. 123-131, 1985.

Ferring Pharmacueticals, SPC for "DESMOTABS," May 18, 2006.

Ferring Pharmacueticals, SPC for "DesmoMelt," Jan. 20, 2006.

Notice of Allowance (including allowed claims) issued on Feb. 23, 2010 U.S. Appl. No. 10/706,100 (US 2004/0138098—Fein).

Office Action issued on Mar. 11, 2010 in U.S. Appl. No. 10/519,715 (US 2007/0117759).

Remington: The Science and Practice of Pharmacy, vol. II, Mack Publishing Company, Easton, PA, 1995,Chapter 85, pp. 1492-1493.

Office Action issued on May 7, 2009, in U.S. Appl. No. 10/519,715 (US 2007/0117759).

U.S. Appl. No. 12/487,116, filed Jun. 18, 2009, Nilsson et al.

U.S. Appl. No. 12/224,437, filed Mar. 1, 2007, Aston.

Office Action issued on Nov. 5, 2007, U.S. Appl. No. 10/519,715 (US 2007/0117759).

Harris, "Clinical experience with desmopressin: Efficacy and safety in central diabetes insipidus and other conditions," *The Journal of Pediatrics*, vol. 114, No. 4, Part 2, pp. 711-718 (Apr. 1989).

Krishnamoorthy et al., "Prodrugs for nasal delivery," *Advanced Drug Delivery Reviews*, vol. 29, pp. 135-146 (1998).

Office Action issued on Aug. 19, 2010 in U.S. Appl. No. 10/519,715 (US 2007/0117759).

* cited by examiner

PHARMACEUTICAL FORMULATIONS

Related Applications

This application is a continuation of U.S. application Ser. No. 10/513,437, filed Jun. 14, 2005, now U.S. Pat. No. 7,560,429, which is a national state entry of Application No. PCT/IB03/02368, filed May 7, 2003.

This invention relates to pharmaceutical formulations, to methods of making them and to their use in the treatment and prophylaxis of diseases in mammals, particularly humans.

Desmopressin (1-desamino-8-D-arginine vasopressin, DDAVP) is an analogue of vasopressin having high antidiuretic activity. It is commercially available as the acetate salt both in tablet form and as a nasal spray, and is commonly prescribed for voiding postponement, incontinence, primary nocturnal enuresis (PNE) and nocturia, among other indications, including central diabetes insipidus.

While existing formulations of desmopressin have met the needs of patients, there is still a need for improvement. Tablets are often preferred by patients because of their ease of use, discretion and the lack of uncertainty of correct administration. However, tablets generally need to be taken with a glass of water or other drink, which is a problem as fluid intake need to be restricted in connection with desmopressin treatment, and the message to the patient is much clearer when there is no water intake at all. Furthermore the bioavailability of desmopressin when taken by tablet is about 0.1% when compared to intravenous injection, a figure which clearly leaves room for improvement.

Intranasal administration leads to higher bioavailability, but is less preferred by patients. Further, intranasal administration may adversely affect the cilia, such that viruses and bacteria may more readily pass into the mucosa.

Sublingual formulations of desmopressin have previously been proposed. Grossman et al., *Br. Med. J.* 1215 (17 May 1980) reported administration of desmopressin in a sublingual lozenge of unspecified composition. In the same year, Laczi et al., *Int. J. Clin. Pharm. Ther. Tox.* 18 (12) 63-68 (1980) reported administration of 30 µg desmopressin in 200 mg sublingual tablets containing sucrose, potato starch, stearin, ethanol (as rectified spirit), white gelatin, distilled water and powdered cocoa. However, in WO-A-8502119 it is stated:

> The so-called sublingual tablet is also objectionable since it requires a relatively long dissolving time and is dependent on a patient's saliva secretion. [WO-A-8502119, page 2, lines 4-6]

Fjellestad-Paulsen et al., *Clin. Endocrinol.* 38 177-82 (1993) administered a liquid nasal spray formulation of desmopressin sublingually, which avoided the problems noted above for the sublingual tablet. However, the authors reported that, following sublingual administration of the liquid, no detectable desmopressin was found in the blood.

It has now been discovered that desmopressin can be administered as a solid orodispersible dosage form which provides improved bioavailability compared to conventional oral tablets of desmopressin.

According to a first aspect of the invention, there is provided an orodispersible pharmaceutical dosage form of desmopressin.

The desmopressin may be in the form of the free base or a pharmaceutically or, where appropriate veterinarily, acceptable salt, or in any other pharmaceutically or veterinarily acceptable form. The acetate salt is particularly preferred.

The formulation will typically be solid. It may disperse rapidly in the mouth, for example within 10, 5, 2 seconds, or even within 1 second, in increasing order of preference. Such formulations are termed 'orodispersible'. The formulation will typically comprise a suitable carrier for this purpose, which will be pharmaceutically acceptable (or veterinarily acceptable in the case of administration to non-human animals).

The daily dosage of desmopressin, measured as the free base, will generally be from 0.5 or 1 µg to 1 mg per dosage form. In one preferred dosage range, the dosage will typically range from 2 µg to 800 µg per dosage form and preferably from 10 µg to 600 µg. Relative low doses are also specifically contemplated, for example from 0.5 µg to 75 µg, preferably 0.5 or 1 µg to 50 µg. When one dosage form per day is administered, as is usual for PNE and nocturia, this will typically be the dose per dosage form. When the daily dose is administered in two or more dosages, as will typically be the case for central diabetes insipidus, the amount of active compound per dosage form will be reduced accordingly.

Other active ingredients, whether or not peptides, may also be present.

Pharmaceutical dosage forms of the present invention are adapted to supply the active ingredient to the oral cavity. The active may be absorbed across the sublingual mucosa, and/or otherwise from the oral cavity (e.g. across the buccal and/or gingival mucosa) and/or from the gastrointestinal tract for systemic distribution.

A variety of formulations are known which are suitable for delivering other active ingredients for absorption from the oral cavity. Such formulations may be useful in the present invention. Among them are intrabuccally disintegrating solid formulations or preparations which comprise the active ingredient, a sugar comprising lactose and/or mannitol and 0.12 to 1.2 w/w %, based on the solid components, of agar and which has a density of 400 mg/ml to 1,000 mg/ml and have a sufficient strength for handling, which in practice may mean sufficient strength to withstand removal from a blister packaging without disintegrating. Such formulations, and how to make them, are disclosed in U.S. Pat. No. 5,466,464, to which reference is made for further details.

In this embodiment of the invention, the sugar may be used in the formulation in an amount of at least 50 w/w %, preferably 80 w/w % or more, more preferably 90 w/w % or more, based on the total solid components, although it may vary depending on the quality and quantity of the active ingredient to be used.

Though types of agar are not particularly limited, those listed in the Japanese Pharmacopoeia may be used preferably. Examples of the listed agar include agar powders PS-7 and PS-8 (manufactured by Ina Shokuhin).

Agar may be used in an amount of from 0.12 to 1.2 w/w %, preferably from 0.2 to 0.4 w/w %, based on the solid components.

In order to produce a formulation in accordance with this embodiment of the present invention, a sugar comprising lactose and/or mannitol is suspended in an aqueous agar solution, filled in a mould, solidified into a jelly-like form and then dried. The aqueous agar solution may have a concentration of from 0.3 to 2.0%, preferably from 0.3 to 0.8%. The aqueous agar solution may be used in such an amount that the blending ratio of agar based on the solid components becomes 0.12 to 1.2 w/w %, but preferably 40 to 60 w/w % of agar solution based on the solid components.

Other formulations known for delivering active ingredients for absorption from the oral cavity are the dosage forms disclosed in U.S. Pat. No. 6,024,981 and U.S. Pat. No. 6,221,392. They are hard, compressed, rapidly dissolvable dosage forms adapted for direct oral dosing comprising: an active ingredient and a matrix including a non-direct compression filter and a lubricant, said dosage form being adapted to rapidly dissolve in the mouth of a patient and thereby liberate said active ingredient, and having a friability of about 2% or less when tested according to the U.S.P., said dosage form optionally having a hardness of at least about 15 Newtons (N), preferably from 15-50 N. U.S. Pat. No. 6,024,981 and U.S. Pat. No. 6,221,392 disclose further details and characteristics of these dosage forms and how to make them.

Preferably, dosage forms in accordance with this embodiment of the invention dissolve in about 90 seconds or less (preferably 60 seconds or less and most preferably 45 seconds or less) in the patient's mouth. It is also often desirable that the dosage form include at least one particle. The particle would be the active ingredient and a protective material. These particles can include rapid release particles and or sustained release particles.

In a particularly preferred formulation in accordance with this embodiment of the present invention there is provided a hard, compressed, rapidly dissolving tablet adapted for direct oral dosing. The tablet includes particles made of an active ingredient and a protective material. These particles are provided in an amount of between about 0.01 and about 75% by weight based on the weight of the tablet. The tablet also includes a matrix made from a non-direct compression filler, a wicking agent, and a hydrophobic lubricant. The tablet matrix comprises at least about 60% rapidly water soluble ingredients based on the total weight of the matrix material. The tablet has a hardness of between about 15 and about 50 Newtons, a friability of less than 2% when measured by U.S.P. and is adapted to dissolve spontaneously in the mouth of a patient in less than about 60 seconds and thereby liberate said particles and be capable of being stored in bulk.

A very fine grained or powdered sugar known as a non-direct compression sugar may be used as a filler in the matrix of this embodiment the present invention. This material, in part because of its chemical composition and in part because of its fine particle size, will dissolve readily in the mouth in a mater of seconds once it is wetted by saliva. Not only does this mean that it can contribute to the speed at which the dosage form will dissolve, it also means that while the patient is holding the dissolving dosage form in his or her mouth, the filler will not contribute a "gritty" or "sandy" texture thus adversely affecting the organoleptic sensation of taking the dosage form. In contrast, direct compression versions of the same sugar are usually granulated and treated to make them larger and better for compaction. While these sugars are water soluble, they may not be solubilised quickly enough. As a result, they can contribute to the gritty or sandy texture of the dosage form as it dissolves. Dissolution time in the mouth can be measured by observing the dissolution time of the tablet in water at about 37° C. The tablet is immersed in the water without forcible agitation or with minimal agitation. The dissolution time is the time from immersion to substantially complete dissolution of the rapidly water soluble ingredients of the tablet as determined by visual observation.

Particularly preferred fillers, in accordance with the present invention are non-direct compression sugars and sugar alcohols which meet the specifications discussed above. Such sugars and sugar alcohols include, without limitation, dextrose, mannitol, sorbitol, lactose and sucrose. Of course, dextrose, for example, can exist as either a direct compression sugar, i.e., a sugar which has been modified to increase its compressibility, or a non-direct compression sugar.

Generally, the balance of the formulation can be matrix. Thus the percentage of filler can approach 100%. However, generally, the amount of non-direct compression filler useful in accordance with the present invention ranges from about 25 to about 95%, preferably between about 50 and about 95% and more preferably from about 60 to about 95%.

The amount of lubricant used can generally range from between about 1 to about 2.5% by weight, and more preferably between about 1.5 to about 2% by weight. Hydrophobic lubricants useful in accordance with the present invention include alkaline stearates, stearic acid, mineral and vegetable oils, glyceryl behenate and sodium stearyl fumarate. Hydrophilic lubricants can also be used.

Protective materials useful in accordance with this embodiment of the present invention may include any of the polymers conventionally utilized in the formation of microparticles, matrix-type microparticles and microcapsules. Among these are cellulosic materials such as naturally occurring cellulose and synthetic cellulose derivatives; acrylic polymers and vinyl polymers. Other simple polymers include proteinaceous materials such as gelatin, polypeptides and natural and synthetic shellacs and waxes. Protective polymers may also include ethylcellulose, methylcellulose, carboxymethyl cellulose and acrylic resin material sold under the registered trade mark EUDRAGIT by Rhone Pharma GmbH of Weiterstadt, Germany.

In addition to the ingredients previously discussed, the matrix may also include wicking agents, non-effervescent disintegrants and effervescent disintegrants. Wicking agents are compositions which are capable of drawing water up into the dosage form. They help transport moisture into the interior of the dosage form. In that way the dosage form can dissolve from the inside, as well as from the outside.

Any chemical which can function to transport moisture as discussed above can be considered a wicking agent. Wicking agents include a number of traditional non-effervescent disintegration agents. These include, for example, microcrystalline cellulose (AVICEL PH 200, AVICEL PH 101), Ac-Di-Sol (Croscarmelose Sodium) and PVP-XL (a crosslinked polyvinylpyrrolidone); starches and modified starches, polymers, and gum such as arabic and xanthan. Hydroxyalkyl cellulose such as hydroxymethylcellulose, hydroxypropylcellulose and hydroxyopropylmethylcellulose, as well as compounds such as carbopol may be used as well.

The conventional range of non-effervescent disintegrant agents used in conventional tablets can be as high as 20%. However, generally, the amount of disintegration agent used ranges from between about 2 and about 5%, according to the Handbook of Pharmaceutical Excipients.

In accordance with this embodiment of the present invention, the amount of wicking agents used may range from between 2 to about 12% and preferably from between 2 to about 5%.

It is also possible, of course, to include non-effervescent disintegrants which may not act to wick moisture, if desirable. In either event, it is preferable to use either rapidly water soluble, non-effervescent disintegrants or wicking agents and/or to minimize the use of generally non-water soluble wicking agents or non-effervescent disintegrants. Non-rapidly dissolvable, non-rapidly water soluble elements if used in sufficient quantity, can adversely affect the organoleptic properties of the tablets as they dissolve within the mouth and therefore should be minimized. Of course, wicking agents or non-effervescent disintegrants which are rapidly water soluble as discussed herein can be used in greater quantity and they will not add to the grittiness of the formulation during dissolution. Preferred wicking agents in accordance with the present invention include crosslinked PVP, although, the amounts of these must be controlled as they are not rapidly water soluble.

In addition, it may be desirable to use an effervescent couple, in combination with the other recited ingredients to improve the disintegration profile, the organoleptic properties of the material and the like. Preferably, the effervescent couple is provided in an amount of between about 0.5 and about 50%, and more preferably, between about 3 and about 15% by weight, based on the weight of the finished tablet. It is particularly preferred that sufficient effervescent material be provided such that the evolved gas is less than about 30 cm, upon exposure to an aqueous environment.

The term "effervescent couple" includes compounds which evolve gas. The preferred effervescent couple evolve gas by means of a chemical reaction which takes place upon exposure of the effervescent disintegration couple to water and/or to saliva in the mouth. This reaction is most often the result of the reaction of a soluble acid source and an alkali monohydrogencarbonate or other carbonate source. The reaction of these two general compounds produces carbon dioxide gas upon contact with water or saliva. Such water-activated materials must be kept in a generally anhydrous state and with little or no absorbed moisture or in a stable hydrated form, since exposure to water will prematurely disintegrate the tablet. The acid sources may be any which are safe for human consumption and may generally include food acids, acid and hydrite antacids such as, for example: citric, tartaric, malic, fumaric, adipic, and succinics. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included.

In the case of the orally dissolvable tablets in accordance with the present invention, it is preferred that both the amount and the type of disintegration agent, either effervescent or non-effervescent, or the combination thereof be provided sufficient in a controlled amount such that the tablet provides a pleasant organoleptic sensation in the mouth of the patient. In some instances, the patient should be able to perceive a distinct sensation of fizzing or bubbling as the tablet disintegrates in the mouth. In general, the total amount of wicking agents, non-effervescent disintegrants and effervescent disintegrants should range from 0-50%. However, it should be emphasized that the formulations of the present invention will dissolve rapidly and therefore, the need for disintegrating agents is minimal. As illustrated in the examples, appropriate hardness, friability and dissolution times can be obtained even without effervescent disintegrants or high quantities of wicking agents.

The use of a non-direct compression filler eliminates the need for many conventional processing steps such as granulation and/or the need to purchase more expensive pre-granulated, compressible fillers. At the same time, the resulting dosage form is a balance of performance and stability. It is robust enough to be conventionally produced using direct compression. It is robust enough to be stored or packaged in bulk. Yet, it rapidly dissolves in the mouth while minimizing the unpleasant feel of conventional disintegrating tablets to the extent possible.

Formulations in accordance with this embodiment of the invention may be made by a method including the steps of:

(a) forming a mixture including an active ingredient and a matrix including a non-direct compression filler and a lubricant;

(b) compressing the mixture to form a plurality of hard, compressed, rapidly disintegrable dosage forms including the active ingredient distributed in the orally dissolvable matrix; and optionally (c) storing the dosage forms in bulk prior to packaging. In a preferred embodiment, the dosage forms are then packaged in a lumen of a package such that there is at least one per package. In a preferred particularly preferred embodiment, the dosage forms are then packaged in a lumen of a package such that there more than one per package. Direct compression is the preferred method of forming the dosage forms.

Other formulations known for delivering active ingredients for absorption from the oral cavity are the dosage forms disclosed in U.S. Pat. No. 6,200,604, which comprise an orally administrable medicament in combination with an effervescent agent used as penetration enhancer to influence the permeability of the medicament across the buccal, sublingual, and gingival mucosa. In the context of the present invention, the medicament is desmopressin, which is administered in some embodiments across the sublingual mucosa. In the formulations of this embodiment of the invention, effervescent agents can be used alone or in combination with other penetration enhancers, which leads to an increase in the rate and extent of oral absorption of an active drug.

Formulations or dosage forms in accordance with this embodiment of the invention should include an amount of an effervescent agent effective to aid in penetration of the drug across the oral mucosa. Preferably, the effervescent is provided in an amount of between about 5% and about 95% by weight, based on the weight of the finished tablet, and more preferably in an amount of between about 30% and about 80% by weight. It is particularly preferred that sufficient effervescent material be provided such that the evolved gas is more than about 5 $cm^3$ but less than about 30 $cm^3$, upon exposure of the tablet to an aqueous environment.

The term "effervescent agent" includes compounds which evolve gas. The preferred effervescent agents evolve gas by means of a chemical reaction which takes place upon exposure of the effervescent agent (an effervescent couple) to water and/or to saliva in the mouth. This reaction is most often the result of the reaction of a soluble acid source and a source of carbon dioxide such as an alkaline carbonate or bicarbonate. The reaction of these two general compounds produces carbon dioxide gas upon contact with water or saliva. Such water-activated materials must be kept in a generally anhydrous state and with little or no absorbed moisture or in a stable hydrated form, since exposure to water will prematurely disintegrate the tablet. The acid sources may be any which are safe for human consumption and may generally include food acids, acid and hydrite antacids such as, for example: citric, tartaric, amalic, fumeric, adipic, and succinics. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included.

The effervescent agent(s) useful in this embodiment of the present invention is not always based upon a reaction which forms carbon dioxide. Reactants which evolve oxygen or other gasses which are safe for human consumption are also considered within the scope. Where the effervescent agent includes two mutually reactive components, such as an acid source and a carbonate source, it is preferred that both components react completely. Therefore, an equivalent ratio of components which provides for equal equivalents is preferred. For example, if the acid used is diprotic, then either twice the amount of a mono-reactive carbonate base, or an equal amount of a di-reactive base should be used for complete neutralization to be realised. However, in other embodiments of the present invention, the amount of either acid or carbonate source may exceed the amount of the other component. This may be useful to enhance taste and/or performance of a tablet containing an overage of either component. In this case, it is acceptable that the additional amount of either component may remain unreacted.

Such dosage forms may also include in amounts additional to that required for effervescence a pH adjusting substance. For drugs that are weakly acidic or weakly basic, the pH of the aqueous environment can influence the relative concentrations of the ionised and unionised forms of the drug present in solution according to the Henderson-Hasselbach equation. The pH solutions in which an effervescent couple has dissolved is slightly acidic due to the evolution of carbon dioxide. The pH of the local environment, e.g. saliva in immediate contact with the tablet and any drug that may have dissolved from it, may be adjusted by incorporating in the tablet a pH adjusting substances which permit the relative portions of the ionised and unionised forms of the drug to be controlled. In this way, the present dosage forms can be optimised for each specific drug. If the unionised drug is known or suspected to be absorbed through the cell membrane (transcellular absorption) it would be preferable to alter the pH of the local environment (within the limits tolerable to the subject) to a level that favours the unionised form of the drug. Conversely, if the ionised form is more readily dissolved the local environment should favour ionisation.

The aqueous solubility of the drug should preferably not be compromised by the effervescent and pH adjusting substance, such that the dosage forms permit a sufficient concentration of the drug to be present in the unionised form. The percentage of the pH adjusting substance and/or effervescent should therefore be adjusted depending on the drug.

Suitable pH adjusting substance for use in the present invention include any weak acid or weak base in amounts additional to that required for the effervescence or, preferably, any buffer system that is not harmful to the oral mucosa. Suitable pH adjusting substance for use in the present invention include, but are not limited to, any of the acids or bases previously mentioned as effervescent compounds, disodium hydrogen phosphate, sodium dihydrogen phosphate and the equivalent potassium salt.

The dosage form of this embodiment of the invention preferably includes one or more other ingredients to enhance the absorption of the pharmaceutical ingredient across the oral mucosa and to improve the disintegration profile and the organoleptic properties of the dosage form. For example, the area of contact between the dosage form and the oral mucosa, and the residence time of the dosage form in the oral cavity can be improved by including a bioadhesive polymer in this drug delivery system. See, for example, Mechanistic Studies on Effervescent-Induced Permeability Enhancement by Jonathan Eichman (1997), which is incorporated by reference herein. Effervescence, due to its mucus stripping properties, would also enhance the residence time of the bioadhesive, thereby increasing the residence time for the drug absorption. Non-limiting examples of bioadhesives used in the present invention include, for example, Carbopol 934 P, Na CMC, Methocel, Polycarbophil (Noveon AA-1), HPMC, Na alginate, Na Hyaluronate and other natural or synthetic bioadhesives.

In addition to the effervescence-producing agents, a dosage form according to this embodiment of the present invention may also include suitable non-effervescent disintegration agents, Non-limiting examples of non-effervescent disintegration agents include: microcrystalline, cellulose, croscarmelose sodium, crospovidone, starches, corn starch, potato starch and modified starches thereof, sweeteners, clays, such as bentonite, alginates, gums such as agar, guar, locust bean, karaya, pectin and tragacanth. Disintegrants may comprise up to about 20 weight percent and preferably between about 2 and about 10% of the total weight of the composition.

In addition to the particles in accordance with this embodiment of the present invention, the dosage forms may also include glidants, lubricants, binders, sweeteners, flavouring and colouring components. Any conventional sweetener or flavouring component may be used. Combinations of sweeteners, flavouring components, or sweeteners and flavouring components may likewise be used.

Examples of binders which can be used include acacia, tragacanth, gelatin, starch, cellulose materials such as methyl cellulose and sodium carboxy methyl cellulose, alginic acids and salts thereof, magnesium aluminium silicate, polyethylene glycol, guar gum, polysaccharide acids, bentonites, sugars, invert sugars and the like. Binders may be used in an amount of up to 60 weight percent and preferably about 10 to about 40 weight percent of the total composition.

Colouring agents may include titanium dioxide, and dyes suitable for food such as those known as F.D.& C. dyes and natural coloring agents such as grape skin extract, beet red powder, beta-carotene, annato, carmine, turmeric, paprika, etc. The amount of colouring used may range from about 0.1 to about 3.5 weight percent of the total composition.

Flavours incorporated in the composition may be chosen from synthetic flavours oils and flavouring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavours are vanilla, citrus oil, including lemon, orange, grape, lime and grapefruit, and fruit essences, including apple, pear, peach, strawberry, raspberry, cherry, plum, pineapple, apricot and so forth. Flavours which have been found to be particularly useful include commercially available orange, grape, cherry and bubble gum flavours and mixtures thereof. The amount of flavouring may depend on a number of factors, including the organoleptic effect desired. Flavours may be present in an amount ranging from about 0.05 to about 3 percent by weight based upon the weight of the composition. Particularly preferred flavours are the grape and cherry flavours and citrus flavours such as orange.

One aspect of the invention provides a solid, oral tablet dosage form suitable for sublingual administration. Excipient fillers can be used to facilitate tableting. The filler desirably will also assist in the rapid dissolution of the dosage form in the mouth. Non-limiting examples of suitable fillers include: mannitol, dextrose, lactose, sucrose, and calcium carbonate.

As described in U.S. Pat. No. 6,200,604, tablets can either be manufactured by direct compression, wet granulation or any other tablet manufacturing technique. The dosage form may be administered to a human or other mammalian subject by placing the dosage form in the subject's mouth and holding it in the mouth, beneath the tongue (for sublingual administration). The dosage form spontaneously begins to disintegrate due to the moisture in the mouth. The disintegration, and particularly the effervescence, stimulates additional salivation which further enhances disintegration.

Although the above described formulations are within the scope of the present invention, the most preferred orodispersible solid pharmaceutical dosage forms according to the invention comprise desmopressin and an open matrix network carrying the desmopressin, the open matrix network being comprised of a water-soluble or water-dispersible carrier material that is inert towards desmopressin.

Pharmaceutical dosage forms comprising open matrix networks are known from GB-A-1548022, to which reference is made for further details. Pharmaceutical dosage forms of the invention can be rapidly disintegrated by water. By "rapidly disintegrated" is meant that the shaped articles are disintegrated in water within 10 seconds. Preferably the shaped article disintegrates (dissolves or disperses) within 5 seconds or even two seconds or one second or less. The disintegration time is measured by a procedure analogous to the Disintegration Test for Tablets, B.P. 1973. The procedure is described in GB-A-1548022 and outlined below.

Apparatus

A glass or suitable plastic tube 80 to 100 mm long, with an internal diameter of about 28 mm and an external diameter of 30 to 31 mm, and fitted at the lower end, so as to form a basket, with a disc of rustproof wire gauze complying with the requirements for a No. 1.70 sieve.

A glass cylinder with a flat base and an internal diameter of about 45 mm containing water not less than 15 cm deep at a temperature between 36° and 38° C.

The basket is suspended centrally in the cylinder in such a way that it can be raised and lowered repeatedly in a uniform manner so that at the highest position the gauze just breaks the surface of the water and at the lowest position the upper rim of the basket just remains clear of the water.

Method

Place one shaped article in the basket and raise and lower it in such a manner that the complete up and down movement is repeated at a rate equivalent to thirty times a minute. The shaped articles are disintegrated when no particle remains above the gauze which would not readily pass through it. No such particle should remain after 10 seconds.

By the term "open matrix network" there is meant a network of water-soluble or water-dispersible carrier material having interstices dispersed throughout. The open matrix network of carrier material is of generally low density. For example the density may be within the range 10 to 200 mg/cc e.g. 10 to 100 mg/cc, preferably 30 to 60 mg/cc. The density of the shaped article may be affected by the amount of active ingredient, or any other ingredients, incorporated into the article and may be outside the above mentioned preferred limits for the density of the matrix network. The open matrix network which is similar in structure to a solid foam enables a liquid to enter the product through the interstices and permeate through the interior. Permeation by aqueous media exposes the carrier material of both the interior and exterior of the product to the action of the aqueous media whereby the network of carrier material is rapidly disintegrated. The open matrix structure is of a porous nature and enhances disintegration of the product as compared with ordinary solid shaped pharmaceutical dosage forms such as tablets, pills, capsules, suppositories and pessaries. Rapid disintegration results in rapid release of the active ingredient carried by the matrix.

The carrier material used in the product of the invention may be any water-soluble or water-dispersible material that is pharmacologically acceptable or inert to the chemical and which is capable of forming a rapidly disintegratable open matrix network. It is preferred to use water-soluble material as the carrier since this results in the most rapid disintegration of the matrix when the product is placed in an aqueous medium. A particularly advantageous carrier may be formed from polypeptides such as gelatin, particularly gelatin which is particularly hydrolysed, e.g. by heating in water. For example, the gelatin may be partially hydrolysed by heating a solution of the gelatin in water, e.g. in an autoclave at about 120° C. for up to 2 hours, e.g. from about 5 minutes to about 1 hour, preferably from about 30 minutes to about 1 hour. The hydrolysed gelatin is preferably used at concentrations of about 1 to 6% or 8% weight/vol., most preferably at 2 to 4% e.g. about 3%, or at 4 to 6% e.g. about 5%. As is apparent from the Examples herein, these concentrations refer to the total formulation prior to removal of the water for example by freeze drying.

Although mammalian derived gelatin may be used, it has an unpleasant taste and thus necessitates the use of sweeteners and flavours to mask the taste of the gelatin in addition to any sweeteners and flavours which may be required to mask the taste of the active ingredient. Moreover, the heating step necessary with the use of mammalian gelatin increases processing times and incurs heating costs thereby increasing the overall costs of the process. Therefore, the use of fish gelatin, especially non-gelling fish gelatin, is preferred, especially for desmopressin. Reference is made to WO-A-0061117 for further details.

Other carrier materials may be used in place of partially hydrolysed gelatin or fish gelatin, for example polysaccharides such as hydrolysed dextran, dextrin and alginates (e.g. sodium alginate) or mixtures of above mentioned carriers with each other or with other carrier materials such as polyvinyl alcohol, polyvinylpyrrolidine or acacia. Modified starch may also be used in place of gelatin, as described in WO-A-0044351, to which reference is made for further details.

Other carrier materials which may be present in addition to, or in some cases in place of, the above carriers include: gums such as tragacanth, xanthan, carageenan, and guar; mucilages including linseed mucilage and agar; polysaccharides and other carbohydrates such as pectin and starch and its derivatives, particularly soluble starch and dextrates; water soluble cellulose derivatives, such as hydroxyethylmethyl cellulose, hydroxypropylmethyl cellulose and hydroxypropyl cellulose; and carbomer.

A filler may also be present. The filler desirably will also assist in the rapid dissolution or dispersion of the dosage form in the mouth. Non-limiting examples of suitable fillers include sugars such as mannitol, dextrose, lactose, sucrose and sorbitol. The filler is preferably used at concentrations of about 0 to 6% or 8% weight/vol., most preferably at 2 to 4% e.g. about 3%, or at 4 to 6% e.g. about 5%. Again, these concentrations refer to the total formulation prior to removal of the water for example by freeze drying.

Pharmaceutical dosage forms of the invention may be in the form of shaped articles. They may incorporate ingredients in addition to the active ingredient(s). For example the pharmaceutical dosage form of the present invention may incorporate pharmaceutically acceptable adjuvants. Such adjuvants include, for example, colouring agents, flavouring agents, preservatives (e.g. bacteriostatic agents), and the like. U.S. Pat. No. 5,188,825 teaches that water soluble active agents should be bonded to an ion exchange resin to form a substantially water insoluble active agent/resin complex; although that teaching may be practised here (for which reference to U.S. Pat. No. 5,188,825 is made for further details), it has been found in the development of the present invention that water soluble peptides such as desmopressin may be formulated in solid dosage forms of the invention without the need for bonding to an ion exchange resin. Such dosage forms may therefore be free of an ion exchange resin. For hydrophobic peptides, which desmopressin is not, a surfactant may be present, as taught in U.S. Pat. No. 5,827,541, to which reference is made for further details. For peptides with an unpleasant taste (which desmopressin does not have), a lipid such as a lecithin may be present to improve patient acceptability, as taught in U.S. Pat. No. 6,156,339, to which reference is made for further details. Other strategies for taste masking include conversion of a soluble salt to a less soluble salt or to the free base, as taught by U.S. Pat. No. 5,738,875 and U.S. Pat. No. 5,837,287, and the use of a process disclosed in U.S. Pat. No. 5,976,577 wherein, prior to freeze drying, a suspension of uncoated or coated coarse particles of the pharmaceutically active substance(s) in a carrier material is cooled to reduce the viscosity and minimize release of the active substance during processing, as well as beyond the point of disintegration of the form in the mouth, to minimise bad taste from the peptide; reference is made to the cited patents for further details.

For insoluble or poorly soluble peptides having a large particle size, xanthan gum may be present, particularly when the carrier is formed from gelatin, as the xanthan gum may act as a gelatin flocculating agent, as disclosed in U.S. Pat. No. 5,631,023, to which reference is made for further details.

As taught by WO-A-9323017 one or more amino acids having from about 2 to 12 carbon atoms may be present, when the matrix is selected from the group consisting of gelatin, pectin, soy fibre protein and mixtures thereof. In this formulation the preferred amino acid is glycine, while the preferred matrix forming agent is gelatin and/or pectin; in a particularly preferred embodiment, the dosage form additionally comprises mannitol.

All excipients will be chosen to be pharmaceutically acceptable.

Pharmaceutical dosage forms of the present invention may be prepared by a process as described in GB-A-1548022, which comprises subliming solvent from a composition comprising the pharmaceutical substance and a solution of the carrier material in a solvent, the composition being in the solid state in a mould.

The sublimation is preferably carried out by freeze drying a composition comprising the active ingredient and a solution of the carrier material in a solvent. The composition may include additional ingredients, such as those mentioned above. The solvent is preferably water but it may contain a co-solvent (such as an alcohol e.g. tert-butyl alcohol) to improve the solubility of the chemical. The composition may also contain a surfactant e.g. Tween 80 (polyoxyethylene (20) sorbitan mono-oleate). The surfactant may help to prevent the freeze dried product sticking to the surface of the mould. It may also aid in the dispersion of the active ingredient.

The composition may contain a pH adjusting agent to adjust the pH of a solution from which the dosage form is prepared within the range of from 3 to 6, preferably from 3.5 to 5.5, and most preferably from 4 to 5, for example 4.5 or 4.8. Citric acid is a preferred pH adjusting agent, but others including hydrochloric acid, malic acid can be used. Such non-volatile pH adjusting agents will not be removed by the freeze drying or other sublimation process and so may be present in the final product.

The mould may comprise a series of cylindrical or other shape depressions in it, each of a size corresponding to the desired size of the shaped article. Alternatively, the size of the depression in the mould may be larger than the desired size of the article and after the contents have been freeze dried the product can be cut into the desired size (for example thin wafers).

However, as described in GB-A-2111423, the mould is preferably a depression in a sheet of filmic material. The filmic material may contain more than one depression. The filmic material may be similar to that employed in conventional blister packs which are used for packaging oral contraceptive tablets and like medicament forms. For example the filmic material may be made of thermoplastic material with the depressions formed by thermoforming. The preferred filmic material is a polyvinyl chloride film. Laminates of filmic material may also be used.

In one embodiment the mould comprises a metal plate (e.g. an aluminium plate) containing one or more depressions. In a preferred process using such a mould, the mould is cooled with a cooling medium (e.g. liquid nitrogen or solid carbon dioxide). When the mould is cooled a predetermined amount of water containing the carrier material, the active ingredient and any other desired ingredient is fed into the depression(s). When the contents of the depression(s) are frozen the mould is subjected to reduced pressure and, if desired, controlled application of heat to aid the sublimation. The pressure can be below about 4 mm. Hg; GB-A-1548022 teaches that employment of pressures of below 0.3 mm Hg, for example 0.1 to 0.2 mm is preferred. The freeze dried products may then be removed from the depressions in the mould and stored for future use, e.g. in airtight jars or other suitable storage containers. Alternatively, the freeze dried product may be enclosed by filmic material as described in GB-A-2111423

A later developed process useful for making pharmaceutical dosage forms in accordance with the invention is described in GB-A-2111423, to which reference is made for further details. The process comprises filling a composition comprising a predetermined amount of active ingredient and a solution of partially hydrolysed gelatin into a mould, freezing the composition in the mould by passing gaseous cooling medium over the mould and then subliming solvent from the frozen composition so as to produce a network of partially hydrolysed gelatin carrying the active ingredient.

In order to help ensure an even thickness of product, the side wall or walls of the mould may diverging outwards from the base and making an angle with the vertical of at least 5° at the surface of the composition, as described in GB-A-2119246 to which reference is made for further details.

Alternatively or in addition, pharmaceutical dosage forms of the present invention may be prepared by a process as described in GB-A-2114440 which comprises freezing a composition comprising a solution in a first solvent of a water-soluble or water-dispersible carrier material that is inert towards the active ingredient, subliming the first solvent from the frozen composition so as to produce a product having a network of carrier material, adding to said product a solution or suspension of a second non-aqueous solvent containing a predetermined amount of the active ingredient and allowing or causing the second solvent to evaporate. Reference is made to GB-A-2114440 for further details.

Alternatively or in addition, pharmaceutical dosage forms of the present invention may be prepared by a process as described in GB-A-2111184, which comprises introducing the liquid medium in the form of droplets beneath the surface of a cooling liquid which is maintained at a temperature lower than the freezing point of the liquid medium, the cooling liquid being immiscible with, and inert with respect to, the liquid medium and having a density greater than that of both the liquid medium and the resulting frozen particles such that as the liquid droplets float upwards in the cooling liquid towards the surface thereof, they are frozen to form spherical particles. The frozen spherical particles can be collected at or near the upper surface of the cooling liquid. Reference is made to GB-A-2111184 for further details.

Dosage forms in accordance with the invention have improved bioavailability. They are intended to be taken orally, and are highly suitable for that purpose. They disperse rapidly in the mouth, and may for example be placed under the tongue (sub-lingually), or they may be placed on the tongue or against the cheek or gingiva.

According to a second aspect of the invention, there is provided a dosage form as described above for use in medicine, particularly, for voiding postponement, incontinence, primary nocturnal enuresis (PNE), nocturia and central diabetes insipidus.

The invention provides a method of postponing voiding, treating or preventing incontinence, primary nocturnal enuresis (PNE), nocturia and/or central diabetes insipidus, the method comprising administering an effective and generally non-toxic amount of desmopressin to a subject in an orodispersible pharmaceutical dosage form, for example in a dosage form as described above. Any other disease or condition treatable or preventable by desmopressin may similarly be addressed by means of the invention. The invention therefore extends to the use of desmopressin in the manufacture of an orodispersible pharmaceutical formulation. The invention also extends to a pack comprising an orodispersible pharmaceutical dosage form of desmopressin together with instructions to place the dosage form in a patient's mouth. Encompassed within the invention is also a method for preparing a packaged dosage form of desmopressin, the method comprising bringing into association an orodispersible pharmaceutical dosage form of desmopressin and instructions to place the dosage form in a patient's mouth. The instructions may for example be printed on packaging encompassing the dosage form when sold or dispensed, or may be on a product information leaflet or insert within the packaging.

Other peptides apart from desmopressin are formulatable in the formulations described above. The invention therefore extends to a orodispersible pharmaceutical dosage form of a pharmaceutically active peptide.

According to a further aspect of the invention, there is provided a solid pharmaceutical dosage form, for example for oral administration, the dosage form comprising a pharmaceutically active peptide and an open matrix network carrying the peptide, the open matrix network being comprised of a water-soluble or water-dispersible carrier material that is inert towards the peptide.

Although oral vaccines made from fast dissolving dosage forms are known from WO-A-9921579, there is no disclosure of pharmaceutically active peptides retaining their activity after administration. The experimental work in WO-A-9921579 merely shows the presence in saliva of IgA antibodies to tetanus toxoid following the administration of tetanus toxoid by means of an adjuvanted fast dissolving dosage vaccine formulation. Formulations of the present invention are not vaccines and do not include adjuvants.

Pharmaceutical dosage forms of this aspect of the invention contain a pharmaceutically active peptide. Such peptides may be directly active per se or they may have one or more active metabolites, i.e. they may be prodrugs for the primary or true active principle. The peptides may have for example from 2 to 20, preferably from 5 to 15, amino acid residues (at least some of which may be D-isomers, although L-isomers will generally be predominant). The peptides may be linear, branched or cyclic, and may include natural residues or substituents or residues or substituents not found in natural peptides or proteins either commonly or at all. Pharmaceutically acceptable salts, simple adducts and tautomers are included where appropriate.

Examples of peptides usefully formulated by means of the invention include somatostatin and its analogues including Cyclo(MeAla-Tyr-D-Trp-Lys-Val-Phe) and Cyclo(Asn-Phe-Phe-D-Trp-Lys-Thr-Phe-GABA), enkephalins including Met$^5$-enkephalin and Leu$^5$-enkephalin, oxytocin analogues such as atosiban (1-deamino-2-D-Tyr-(OEt)-4-Thr-8-Orn-oxytocin), GNRH analogues such as triptorelin (6-D-Trp-GnRH), leuprolide ([D-Leu$^6$, Pro$^8$-NHEt]-GnRH), degarelix (Ac-D-2NaI-D-4 Cpa-D-3 Pal-Ser-4Aph(L-Hydroorotyl)-D-4Aph(Cbm)-Leu-Ilys-Pro-D-Ala-NH$_2$, where 2NaI is 2-naphthylalanine, 4 Cpa is 4-chlorophenylalanine, 3Pal is 3-pyridylalanine, ILys is N(ε)-isopropyllysine, 4Aph is 4-aminophenylalanine and Cbm is the carbamoyl group) and other GnRH antagonists disclosed in U.S. Pat. No. 5,925,730 and U.S. Pat. No. 4,072,668, and vasopressin analogues such as desmopressin. It is particularly preferred to formulate by means of the invention agonists of naturally active peptides, such as those described above, since agonists may be active at lower doses than antagonists.

Dosage will be as determined by the physician or clinician, depending on the nature of the peptide, the nature of the disease or condition being treated or prevented, and other factors.

The invention extends to the use of a peptide in the manufacture of a dosage form as described above for treating or preventing a disease or condition which is treatable or preventable by a peptide.

The invention also provides a method of treating or preventing a disease or condition which is treatable or preventable by a peptide, the method comprising administering an effective and generally non-toxic amount of the peptide to a subject in a dosage form as described above.

The contents of each of the documents referred to in this specification are incorporated herein by reference to the fullest extent allowed by law.

Preferred features of each aspect of the invention, and where feasible and appropriate each embodiment of each aspect of the invention, are as for each other aspect or embodiment, mutatis mutandis. In particular, it is contemplated that aspects, features and embodiments of the invention described above specifically in relation to desmopressin are applicable also to other peptides.

The invention will now be illustrated by the following examples.

EXAMPLE 1

200 μg Desmopressin Orodispersible Dosage Form

Spray-dried fish gelatin (4 g) and mannitol (3 g) are added to a glass beaker. Purified water (93 g) is then added and solution effected by stirring using a magnetic follower. The pH is checked and adjusted to 4.8 with citric acid as necessary.

A Gilson pipette can then be used to deliver 500 mg of this solution into each one of a series of pre-formed blister pockets having a pocket diameter of about 16 mm. The blister laminate may comprise PVC coated with PVdC. The dosed units are then frozen at a temperature of −110° C. in a freeze tunnel with a residence time of 3.2 minutes and the frozen units are then held in an upright freezer for a time greater than 1.5 hours at a temperature of −25° C. (5° C.). The units are then freeze-dried overnight with an initial shelf temperature of 10° C. rising to +20° C. at a pressure of 0.5 mbar. The units can be checked for moisture prior to unloading by the drying trace and by the pressurised moisture check.

In this way, following the general procedure given in Example 1 of WO-A-0061117, a desmopressin orodispersible dosage form is prepared using the following ingredients per unit dosage form:

| | |
|---|---|
| Desmopressin (PolyPeptide Laboratories, Sweden) | 200 μg |
| Mannitol EP/USP (Roquette, Mannitol 35) | 15 mg |
| Fish gelatin USNF/EP | 20 mg |
| Citric acid (if necessary) [pH adjusting agent] | q.s. to pH 4.8 |
| Purified water | [Removed during processing] |

EXAMPLE 2

400 μg Desmopressin Orodispersible Dosage Form

The procedure of Example 1 herein is followed, except that the amount of desmopressin per unit dosage form was 400 μg.

EXAMPLE 3

800 μg Desmopressin Orodispersible Dosage Form

The procedure of Example 1 herein is followed, except that the amount of desmopressin per unit dosage form was 800 μg.

EXAMPLE 4

200 μg Desmopressin Orodispersible Dosage Form

Following the general procedure given in Example 1 of WO-A-0061117, a desmopressin dosage form orodispersible dosage form was prepared using the following ingredients per unit dosage form:

| | |
|---|---|
| Desmopressin (PolyPeptide Laboratories, Sweden) | 200 μg |
| Mannitol EP/USP (Roquette, Mannitol 35) | 6 mg |
| Fish gelatin USNF/EP | 10 mg |
| Citric acid (if necessary) [pH adjusting agent] | q.s. to pH 4.8 |
| Purified water | [Removed during processing] |

EXAMPLE 5

400 μg Desmopressin Orodispersible Dosage Form

The procedure of Example 4 herein was followed, except that the amount of desmopressin per unit dosage form was 400 μg.

EXAMPLE 6

800 μg Desmopressin Orodispersible Dosage Form

The procedure of Example 4 herein was followed, except that the amount of desmopressin per unit dosage form was 800 μg.

COMPARATIVE EXAMPLE 1

Desmopressin i.v. Solution

An injectable preparation of desmopressin was conventionally prepared using the following ingredients:

| | |
|---|---|
| Desmopressin (PolyPeptide Laboratories, Sweden) | 4 mg |
| Sodium chloride (National Corporation of Swedish Pharmacies, Sweden) | 9 mg |
| Hydrochloric acid (1N) (Merck, Germany) | q.s. to pH 4 |
| Water for injection | q.s. to 1 ml |

COMPARATIVE EXAMPLE 2

200 μg Desmopressin Conventional Tablet

Using a conventional wet granulation process, tablets containing the following ingredients were prepared:

| | |
|---|---|
| Desmopressin (PolyPeptide Laboratories, Sweden) | 200 μg |
| Lactose (Pharmatose 150M, DMV, The Netherlands) | 120 mg |
| Potato starch (Lyckeby AB, Sweden) | 77 mg |
| PVP (Kollidon 25, BASF, Germany) | 1.8 mg |
| Magnesium stearate (Peter Greven, Germany) | 1 mg |
| Granulation Liquid (water, ethanol) | [Removed during processing] |

COMPARATIVE EXAMPLE 3

100 μg Desmopressin Conventional Tablet

The procedure of Comparative Example 2 was followed, except that the amount of desmopressin was 100 μg per tablet.

EXAMPLE 7

Bioavailability of Desmopressin Administered in Accordance with Examples 4 to 6

Study Design

Twenty-four healthy non-smoking male volunteers were enrolled in the present study. The study was designed as a one-centre, open-labelled, randomised, balanced, 4-way cross-over phase I study. Each subject was, in a randomised order, administered sublingually desmopressin as a 200 μg, 400 μg and 800 μg orodispersible dosage form (Examples 4, 5 and 6, respectively) and 2 μg as an i.v. bolus dose (Comparative Example 1). Between the doses there was a washout period of 72 hours. In order to standardise the buccal mucosa before administration of the orodispersible tablet, the subjects were asked to avoid foods, chewing gum etc. Subjects were allowed to brush their teeth in the morning before dosing, but without toothpaste.

Blood Samples

Blood samples for plasma concentration of desmopressin were collected according to the following schedule: pre-dose and 15, 30 and 45 min and at 1, 1.5, 2, 3, 4, 6, 8, 10, 12 and 24 hours post-dosing. After intravenous administration additional blood samples were collected 5 and 10 minutes post-dosing.

Assay

The concentration of desmopressin in plasma was determined by a validated RIA method.

Pharmacokinetic Analysis

The concentration of desmopressin in plasma was analysed for the individual volunteer in each administration group, by use of non-compartmental methods using the commercially available software WinNonlin™ Pro, ver. 3.2 (Pharsight Corporation, US). A plasma concentration value below limit of quantitation (LOQ) followed by values above LOQ was set at 'LOQ/2' for the NCA analysis and for the descriptive statistics on concentrations. Values below LOQ not followed by values above the LOQ are excluded from the NCA analysis, and set to zero in the descriptive statistics on concentrations.

Results of Pharmacokinetic Analysis

After i.v. administration the mean volume of distribution at steady state (Vss) was 29.7 $dm^3$. The mean clearance was calculated to be 8.5 $dm^3$/hr and the mean elimination half-life was determined to be 2.8 hours. After oral administration of desmopressin maximum plasma concentrations were observed at 0.5-2.0 hours after dosing. The maximum plasma concentration was 14.25, 30.21 and 65.25 pg/ml after an oral dose of 200, 400 and 800 μg, respectively. After reaching the maximum value desmopressin was eliminated with a mean elimination half-life in the range of 2.8-3.0 hours. The bioavailability was determined to be 0.30% with at 95% confidence interval of 0.23-0.38%.

The pharmacokinetics of desmopressin is linear, when administered as the orodispersible dosage form of Example 4, 5 or 6.

COMPARATIVE EXAMPLE 4

Bioavailability of Desmopressin Administered in Accordance with Comparative Examples 2 and 3

Thirty six healthy male volunteers (Caucasian, Black and Hispanic) were enrolled in this study, which was designed as an open label, single dose, 3-way crossover study. Each subject was, in a randomised order, administered 200 μg desmopressin as a single 200 μg tablet (Comparative Example 2), 200 μg desmopressin as two 100 μg tablets (Comparative Example 3) and 2 μg as an i.v. bolus dose (Comparative Example 1).

After i.v. administration the mean elimination half-life was determined to be 2.24 hours. After oral administration of desmopressin maximum plasma concentrations were observed at 1.06 hours (2×100 μg) or 1.05 hours (1×200 μg) after dosing. The maximum plasma concentration was 13.2 and 15.0 pg/ml after an oral dose of 2×100 μg and 1×200 μg, respectively. The bioavailability was determined to be 0.13% (2×100 μg) or 0.16% (1×200 μg).

The invention claimed is:

1. A solid orodispersible pharmaceutical dosage form comprising from 10 to 600 μg desmopressin acetate, measured as the free base, which solid orodispersible dosage form disintegrates in the mouth within 10 seconds.

2. The dosage form as claimed in claim 1, which is adapted for sublingual administration.

3. The dosage form as claimed in claim 1, wherein the dosage form is obtainable by subliming solvent from a composition comprising desmopressin acetate and a solution of carrier material in a solvent, the composition being in the solid state in a mold.

4. The dosage form as claimed in claim 3, wherein the sublimation is carried out by freeze drying a composition comprising desmopressin acetate and a solution of the carrier material in a solvent.

5. The dosage form as claimed in claim 1, which comprises an open matrix network carrying the desmopressin acetate, the open matrix network being comprised of a water-soluble or water-dispersable carrier material that is inert towards desmopressin.

6. The dosage form as claimed in claim 5, wherein the open matrix network comprises gelatin.

7. The dosage form as claimed in claim 6, wherein the gelatin is fish gelatin.

8. The dosage form as claimed in claim 7, wherein the fish gelatin is non-gelling.

9. A pack comprising an orodispersible solid pharmaceutical dosage form as defined in claim 1 together with instructions to place the dosage form in a patient's mouth beneath the tongue (for sublingual administration).

* * * * *